United States Patent
Nariman

(10) Patent No.: US 6,742,168 B1
(45) Date of Patent: May 25, 2004

(54) METHOD AND STRUCTURE FOR CALIBRATING SCATTEROMETRY-BASED METROLOGY TOOL USED TO MEASURE DIMENSIONS OF FEATURES ON A SEMICONDUCTOR DEVICE

(75) Inventor: Homi E. Nariman, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 94 days.

(21) Appl. No.: 10/103,223

(22) Filed: Mar. 19, 2002

(51) Int. Cl.$^7$ .................. G06F 17/50; G06F 19/00; G06K 9/00
(52) U.S. Cl. .................. 716/4; 716/21; 700/109; 700/120; 700/121; 702/83; 702/84; 702/134; 702/172; 356/328; 356/334; 356/336; 356/337; 382/144; 382/145
(58) Field of Search ............... 716/4, 21; 700/109, 700/120, 121; 702/83, 84, 118, 134, 172; 356/328, 334, 336, 337, 237.4, 237.5; 382/144, 145

(56) References Cited

U.S. PATENT DOCUMENTS

| | | | |
|---|---|---|---|
| 5,867,276 A | 2/1999 | McNeil et al. | 356/445 |
| 5,877,680 A | 3/1999 | Border | 356/376 |
| 5,880,838 A | 3/1999 | Marx et al. | 356/351 |
| 6,051,348 A | 4/2000 | Marinaro et al. | 430/30 |
| 6,081,334 A | 6/2000 | Grimbergen et al. | 356/357 |
| 6,245,584 B1 | 6/2001 | Marinaro et al. | 438/14 |
| 6,272,392 B1 | 8/2001 | Capodieci | 700/110 |

(List continued on next page.)

FOREIGN PATENT DOCUMENTS

| | | | |
|---|---|---|---|
| EP | 0 727 715 A1 | 8/1996 | G03F/7/20 |
| WO | WO 02/13232 A2 | 2/2002 | |

OTHER PUBLICATIONS

McGahan et al., "Design and performance of a normal–incidence optical critical dimension metrology system", International Microprocesses and Nanotechnology Conference, Oct. 31, 2001, p. 238.*

Primary Examiner—Matthew Smith
Assistant Examiner—Phallaka Kik
(74) Attorney, Agent, or Firm—Williams, Morgan & Amerson, P.C.

(57) ABSTRACT

The present invention is generally directed to a method and a structure for calibrating a scatterometry-based metrology tool used to measure dimensions of features on a semiconductor device. In one illustrative embodiment, the method comprises measuring a critical dimension of at least one production feature formed above a wafer using a scatterometry tool, measuring at least one of a plurality of grating structures formed above the wafer using the scatterometry tool, each of the grating structures having a different critical dimension, and correcting the measured critical dimension of the at least one production feature based upon the measurement of the at least one grating structure. In further embodiments, the method comprises forming a plurality of production features above a wafer, forming a plurality of grating structures above the wafer, each of the grating structures comprised of a plurality of features each having a target critical dimension that thereby defines a critical dimension of the grating structure, each of the grating structures having a different critical dimension, measuring a critical dimension of at least one of the production features using a scatterometry tool, measuring at least one of the grating structures using the scatterometry tool to determine a measured critical dimension of at least one feature of the at least one grating structure, and correcting the measured critical dimension of the at least one production feature based upon a comparison between the measured critical dimension of the at least one feature on the at least one grating structure and the target critical dimension of the feature on the at least one grating structure.

32 Claims, 3 Drawing Sheets

U.S. PATENT DOCUMENTS

| | | | |
|---|---|---|---|
| 6,433,878 B1 * | 8/2002 | Niu et al. | 356/603 |
| 6,448,097 B1 * | 9/2002 | Singh et al. | 438/16 |
| 6,545,753 B2 * | 4/2003 | Subramanian et al. | 356/237.5 |
| 6,561,706 B2 * | 5/2003 | Singh et al. | 396/611 |
| 6,563,578 B2 * | 5/2003 | Halliyal et al. | 356/237.4 |
| 6,583,871 B1 * | 6/2003 | Rangarajan et al. | 356/237.5 |
| 6,643,008 B1 * | 11/2003 | Stirton et al. | 356/237.5 |
| 6,657,736 B1 * | 12/2003 | Finarov et al. | 356/625 |
| 2002/0012854 A1 | 1/2002 | Peng | 430/5 |
| 2002/0107650 A1 * | 8/2002 | Wack et al. | 702/81 |
| 2002/0131040 A1 * | 9/2002 | Niu et al. | 356/237.5 |
| 2002/0135781 A1 | 9/2002 | Singh et al. | 356/601 |
| 2002/0176074 A1 * | 11/2002 | Hasan | 356/237.5 |

* cited by examiner

METHOD AND STRUCTURE FOR CALIBRATING SCATTEROMETRY-BASED METROLOGY TOOL USED TO MEASURE DIMENSIONS OF FEATURES ON A SEMICONDUCTOR DEVICE

BACKGROUND OF THE INVENTION

1. Field of the Invention

This invention relates generally to semiconductor fabrication technology, and, more particularly, to a method and a structure for calibrating a scatterometry-based metrology tool used to measure dimensions of features on a semiconductor device.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

By way of background, an illustrative field effect transistor 10, as shown in FIG. 1, may be formed above a surface 11A of a semiconducting substrate or wafer 11 comprised of doped-silicon. In the process of forming integrated circuit devices, millions of transistors, such as the illustrative transistor 10 depicted in FIG. 1, are formed above a semiconducting substrate. The substrate 11 may be doped with either N-type or P-type dopant materials, for example. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

During the course of fabricating such integrated circuit devices, a variety of features, e.g., gate electrodes, conductive lines, openings in layers of insulating material, etc., are formed to very precisely controlled dimensions. Such dimensions are sometimes referred to as the critical dimension (CD) of the feature. It is very important in modern semiconductor processing that features be formed as accurately as possible due to the reduced size of those features in such modern devices. The gate electrode 14 has a critical dimension 12, i.e., the width of the gate electrode 14, that approximately corresponds to the channel length 13 of the device when the transistor 10 is operational. Gate electrodes 14 may now be patterned to a width 12 that is approximately 180 nm, and further reductions are planned in the future, e.g., 120 nm. Since the width 12 of the gate electrode 14 corresponds approximately to the channel length 13 of the transistor 10 when it is operational, even slight variations in the critical dimension 12 of the gate electrode 14 as fabricated may adversely affect device performance. Moreover, at a given level of a wafer, features, e.g., gate electrodes, may be formed to a variety of different critical dimensions. Additionally, gate electrodes and/or shallow trench isolation structures at a given level may have differing critical dimensions.

Given the importance of forming features to very precise dimensions, semiconductor manufacturers typically measure the critical dimension of the resulting features to insure that manufacturing operations are producing features with dimensions that are within a previously determined acceptable range. Scatterometry-based metrology tools may be employed in determining the various dimensions. However, in situations where features having a variety of different critical dimensions must be measured, it is important that the metrology data obtained while measuring these structures be accurate, and that the scatterometry tool can be accurately calibrated as part of the overall metrology process.

The present invention is directed to a method and device that may solve, or at least reduce, some or all of the aforementioned problems.

SUMMARY OF THE INVENTION

The present invention is generally directed to a method and a structure for calibrating a scatterometry-based metrology tool used to measure dimensions of features on semiconductor devices. In one illustrative embodiment, the method comprises measuring a critical dimension of at least one production feature formed above a wafer using a scatterometry tool, measuring at least one of a plurality of grating structures formed above the wafer using the scatterometry tool, each of the grating structures having a different critical dimension, and correcting the measured critical dimension of the at least one production feature based upon the measurement of the at least one grating structure.

In another illustrative embodiment, the method comprises forming a plurality of production features above a wafer, forming a plurality of grating structures above the wafer, each of the grating structures comprised of a plurality of features each having a target critical dimension that thereby defines a critical dimension of the grating structure, each of the grating structures having a different critical dimension, measuring a critical dimension of at least one of the production features using a scatterometry tool, measuring at least one of the grating structures using the scatterometry tool to determine a measured critical dimension of at least one feature of the at least one grating structure, and correcting the measured critical dimension of the at least one production feature based upon a comparison between the measured critical dimension of the at least one feature on the at least one grating structure and the target critical dimension of the feature on the at least one grating structure.

BRIEF DESCRIPTION OF THE DRAWINGS

The invention may be understood by reference to the following description taken in conjunction with the accompanying drawings, in which like reference numerals identify like elements, and in which.

Figure 1:
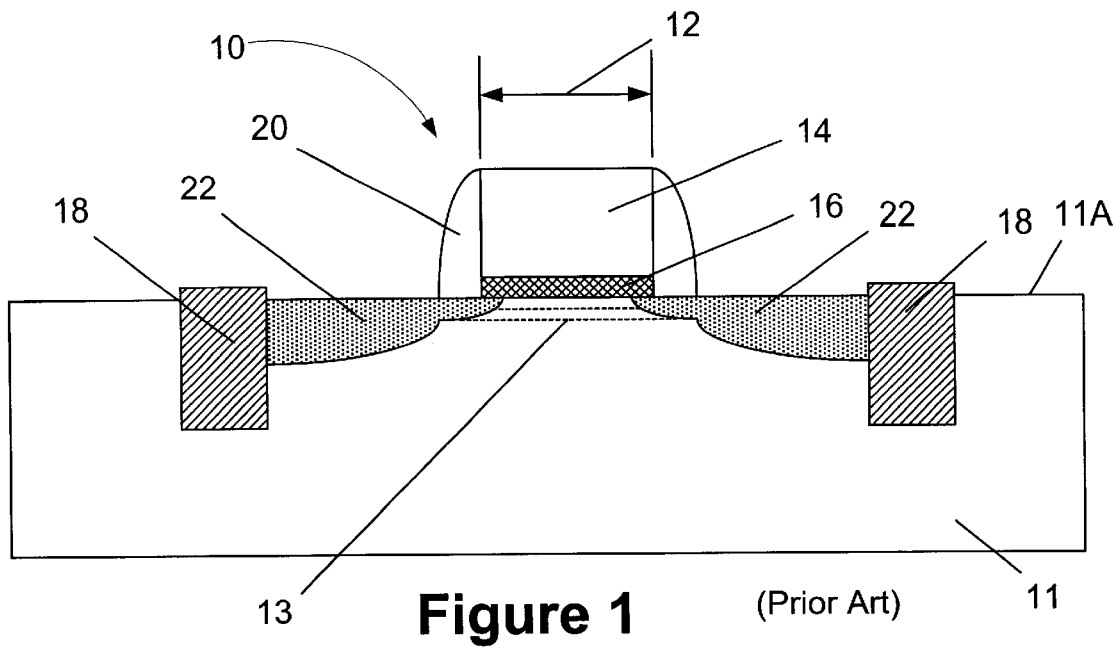
FIG. 1 is a cross-sectional view of an illustrative prior art transistor.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to a method and a structure for calibrating a scatterometry-based metrology tool used to measure dimensions of features on a semiconductor device. As will be readily apparent to those skilled in the art upon a complete reading of the present application, the present method is applicable to obtaining metrology data for a vast variety of different features formed in integrated circuit devices, e.g., the critical dimension of gate electrode structures, the width of shallow trench isolation regions, the width of conductive lines, etc. Thus, the particular feature measured on a semiconductor device should not be considered a limitation of the present invention unless such limitations are expressly set forth in the appended claims.

Figure 2:
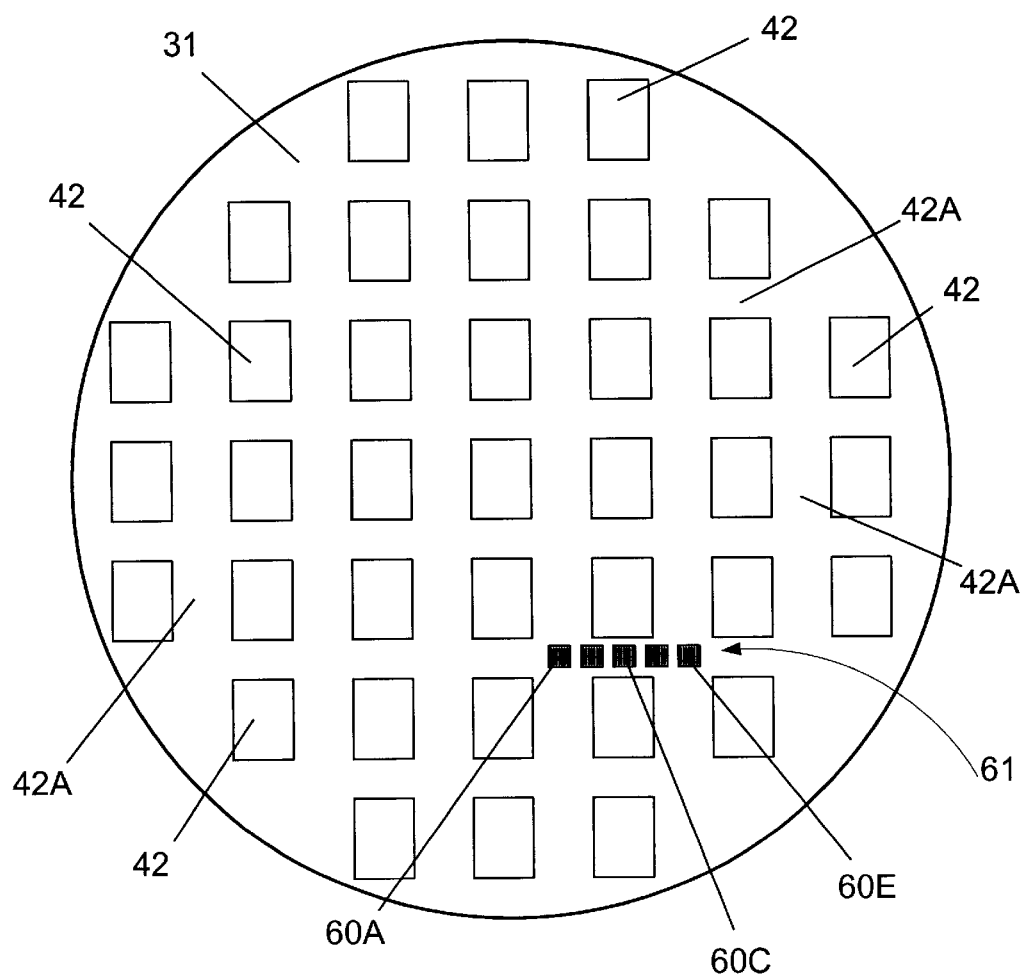
FIG. 2 is a plan view of an illustrative wafer depicting several production die and a plurality of grating structures formed above said wafer.

As shown in FIG. 2, a plurality of production die 42 are formed above a wafer 31. The die 42 define an area of the wafer 31 where production integrated circuit devices, e.g., microprocessors, ASICs, memory devices, etc., will be formed. The size, shape and number of die 42 per wafer 31 depend upon the type of device under construction. For example, several hundred die 42 may be formed above an 8-inch diameter wafer 31. The production die 42 are separated from each other by scribe lines 42A. After the fabrication processes are completed, the wafer 31 will be cut along the scribe lines 42A, and the production die 42, containing the integrated circuit device formed thereon, will be packaged and sold.

In fabricating integrated circuit devices, many features are formed above the wafer 31. Such features may include, but are not limited to, shallow trench isolation structures (STIs), gate electrode structures, conductive metal or polysilicon lines, etc. Moreover, such features may be formed at various levels of the completed integrated circuit device. For example, shallow trench isolations and gate electrode structures are formed at the lowest level, i.e., the device level, while conductive metal lines may be formed at multiple levels above the wafer 31. Additionally, at each level, the features constructed at that level may have differing critical dimensions, e.g., the critical dimensions of the gate electrode structures may vary, the STI structures may have a different critical dimension than that of the gate electrode structures formed at the same level, etc. For example, at the device level, shallow trench isolations may be formed that have a width of approximately 250 nm, while gate electrode structures formed at that level may have a critical dimension of approximately 180 nm. Moreover, similar type structures, e.g., conductive lines, at a given level may have differing nominal widths due to a variety of factors, such as physical plot space limitations or design choice.

The present invention is generally directed to various methods and structures that may be used to calibrate scatterometry-based metrology tools used to measure the critical dimension of these various features. As a general statement, such methodologies involve the use of an illustrative array 61 (see FIGS. 2 and 3) comprised of a plurality of grating structures 60A–E formed above the wafer 31. For ease of reference, the grating structures 60A–E may be referred to individually and/or collectively by the reference numeral 60. As will be recognized by those skilled in the art after a complete reading of the present application, the size, shape, number, location and orientation of the grating structures 60 may be varied depending upon the context in which the invention is employed and on the features to be measured. Moreover, although the illustrative grating structures 60A–E are depicted in a linear array, they may be oriented in a different manner, or individually dispersed around the surface of the wafer 31 in a random manner. The grating structures 60 may be formed in the scribe lines 42A of the wafer 31. Lastly, more than one such array 61 may be formed at a given level of the device, and such multiple arrays 61 may be useful in calibrating a scatterometry tool for measuring features having different nominal feature sizes. For example, a first such array may be adapted for calibrating a scatterometry tool for measurements at a first nominal range, e.g., 220–280 nm, while the second such array may be adapted for calibrating such a scatterometry tool to measure dimensions in the range of 110–70 nm.

Figure 3:
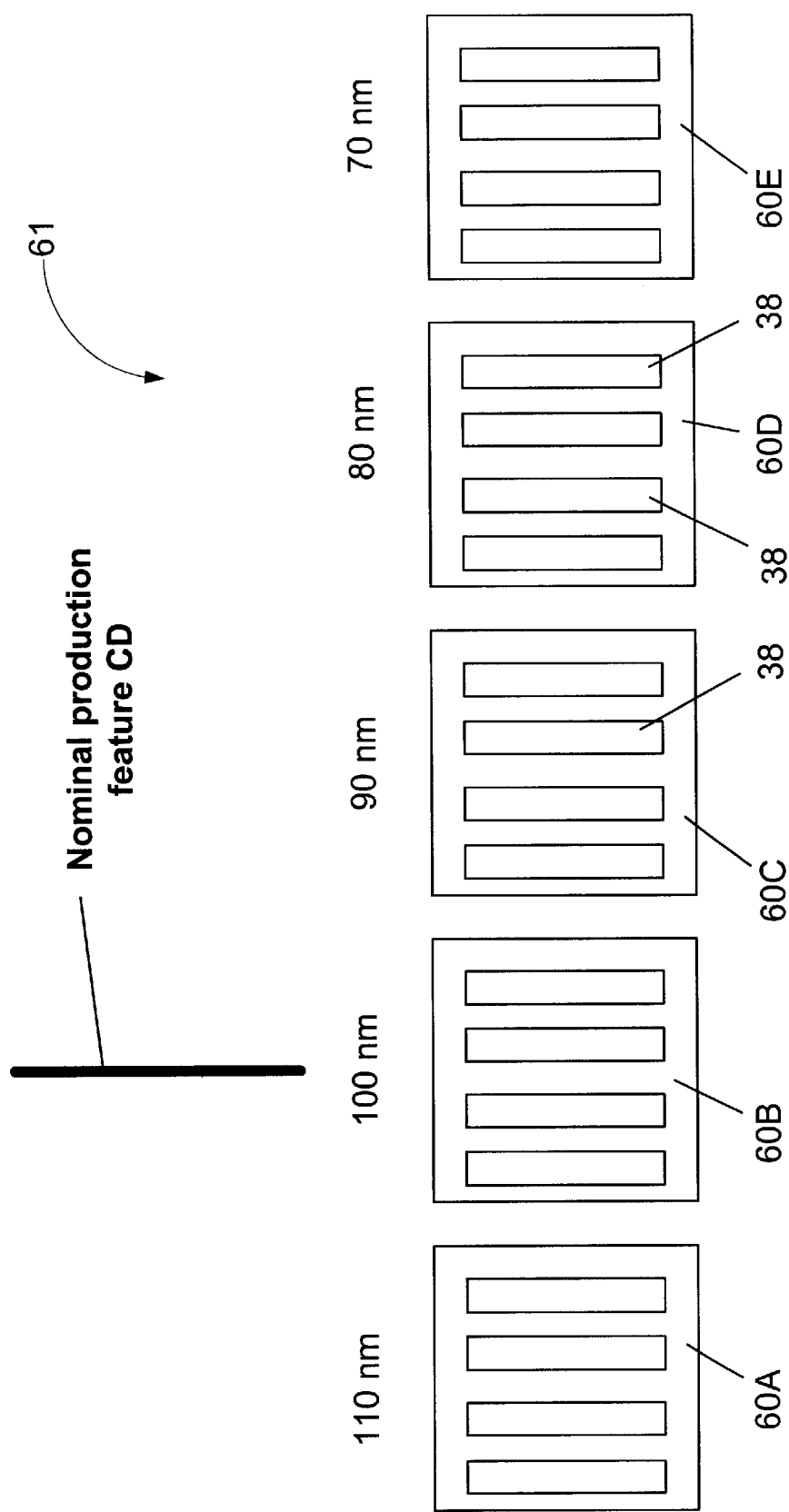
FIG. 3 is an enlarged view of an illustrative array of grating structures that may be employed with the present invention.

FIG. 3 depicts an illustrative array 61 comprised of the illustrative grating structures 60A–E. Each of the grating structures 60A–E is comprised of a plurality of features 38. The features 38 on each of the grating structures 60A–E have different critical dimensions. As set forth previously, the size, shape, and configuration of the grating structures 60A–E may be varied depending upon the features to be measured using a scatterometry tool. The grating structures 60 may be comprised of any type of features 38, e.g., metal lines, STI structures, gate electrode structures, etc. In the case where it is known that a plurality of features will be formed above the wafer 32 to a nominal critical dimension of 100 nm, the grating structures 60A–E may be comprised of features that have critical dimensions that vary about this nominal value by a known amount, i.e., a fixed offset. For example, in one illustrative embodiment depicted in FIG. 3, where the nominal critical dimension of the feature is 100 nm, e.g., gate electrode structures, the array 61 may be comprised of five grating structures 60A–E, each of which is comprised of features having critical dimensions of, respectively, 110 nm, 100 nm, 90 nm, 80 nm and 70 nm. That is, the critical dimension of each grating structure 60A–E is defined by the size of the features 38 that comprise the grating structure 60A–E. The particular size of the critical dimension of the features 38 comprising the grating structure 60A–E and the incremental difference in the critical dimension of the features 38 comprising the grating structure 60 may vary. In the depicted embodiment in FIG. 3, the grating structures 60A–E have a dimensional offset of 10 nm from one grating structure to the next.

Figure 4A:
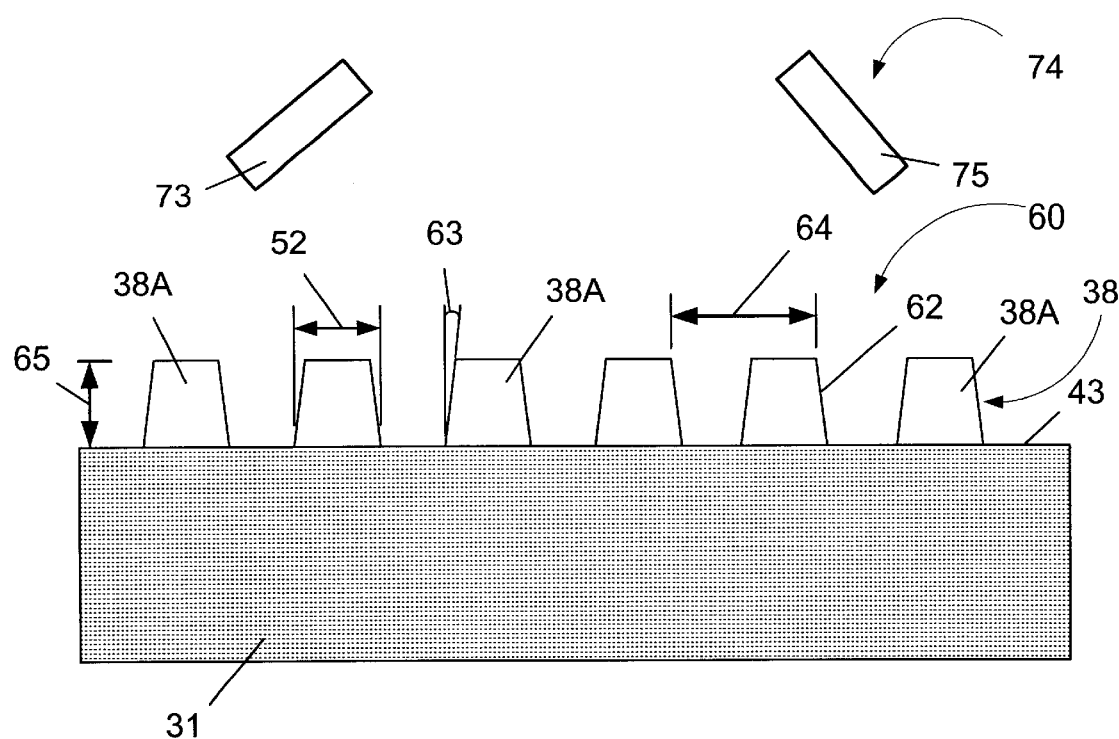
FIGS. 4A–4B depict one illustrative embodiment of an illustrative grating structure that may be employed with the present invention.
Figure 4B:
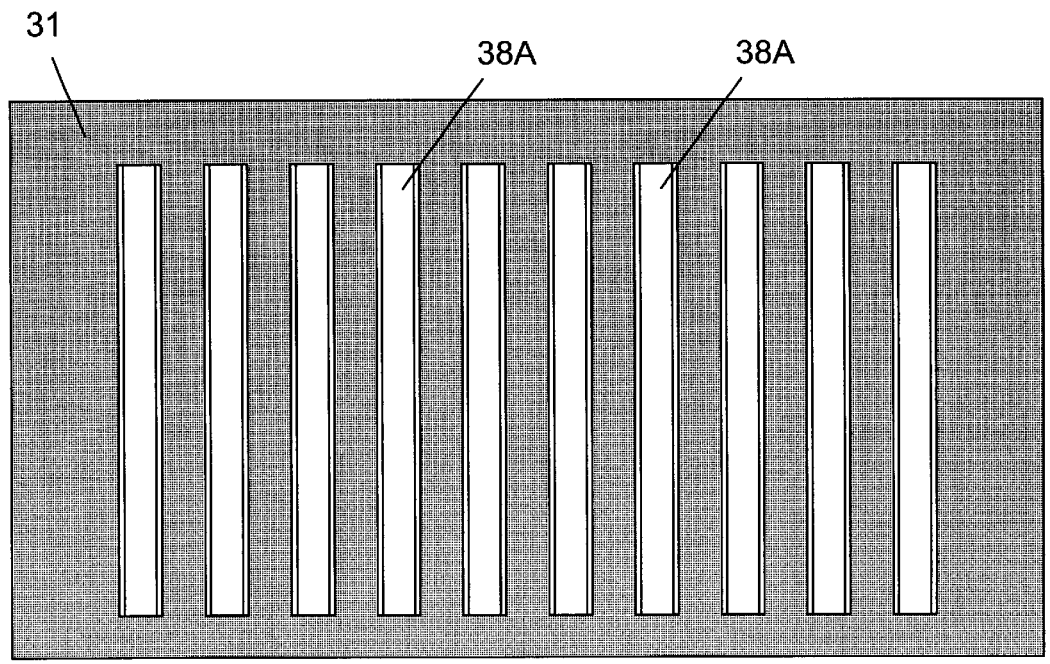

One illustrative grating structure 60, depicted in FIGS. 4A–4B, is comprised of a plurality of gate electrode structures 38A. The gate electrode structures 38A comprising the grating structure 60 have a thickness 65 and sidewalls 62 disposed at an angle 63 (relative to a line normal to the surface 43 of the substrate). The gate electrode structures 38A have a critical dimension 52. The thickness 65, the sidewall angle 63, the pitch 64 of the gate electrode structures 38A, and the critical dimension 52 of the gate electrode structures 38A may be varied as a matter of design choice. The grating structure 60 may be formed in regions having, for example, approximate dimensions of 100 $\mu$m×120 $\mu$m, and it may be comprised of approximately 150–200 gate electrode structures 38A (depending upon the selected pitch). Of course, the features that comprise the grating structures 60A–E will vary depending upon the features to be measured.

Each of the grating structures 60A–E, or the array 61 comprising the grating structures 60, may be formed as a separate test structure that is formed in an area defined by a scribe line 42A of a wafer 31. The features that are part of the grating structure 60 may be formed at the same time that other similar features are being formed for production devices formed on the wafer 31. That is, a pattern for the grating structures 60A–E may be formed in a reticle that will be used in the process of forming production integrated circuit devices within the die 42. Alternatively, a separate reticle may be used to form the features that comprise the grating structures 60A–E.

Typically, the critical dimension 52 of the features 38 comprising the various grating structures 60A–E will be such that at least some of the plurality of grating structures 60A–E will be comprised of features 38 having a critical dimension that is comparable to the intended or nominal critical dimension of features to be formed in manufacturing production devices. That is, the group of grating structures 60A–E will provide a range of critical dimensions of features 38 that may be formed on an integrated circuit device, at least for a given type of feature.

In one illustrative embodiment, the array 61 may be comprised of five grating structures 60A–E. In this embodiment, the first of the grating structures, e.g., 60A, may have features 38 that are a fixed increment above a nominal feature size, while the second grating structure 60B is comprised of features 38 at the approximate nominal feature size, and grating structures 60C–D are comprised of features 38 that are successively smaller than the nominal feature size. For example, for a nominal feature size of 250 nm, e.g., for metal lines, the array 61 may be comprised of grating structures 60A–E having feature sizes of, respectively, 260 nm, 250 nm, 240 nm, 230 nm and 220 nm. Of course, this illustrative array pattern may be varied, e.g., the array 61 may be comprised of grating structures 60A–E having feature sizes of, respectively, 280 nm, 275 nm, 250 nm, 235 nm and 220 nm. Thus, the particular pattern or arrangement of the array 61, as well as the incremental difference in the feature sizes of each grating structure 60A–E, may be varied as a matter of design choice.

Through use of the present invention, scatterometry-based metrology tools may be accurately and reliably calibrated to enhance the accuracy of the critical metrology data obtained by such tools. For example, due to the complexity of modern semiconductor processing tools, there will be variations in the size, e.g., critical dimension, of features formed on a wafer. While scatterometry tools may be accurately calibrated to a known nominal value, in measuring feature sizes that vary from this nominal value, undesirable errors may be introduced into the measurement process. That is, if a scatterometry tool is calibrated to measure critical dimensions having a target value of 100 nm, unwanted errors may be introduced in the measurement process when the scatterometry-based tool is used to measure critical dimensions above or below this value by a significant amount. The present invention provides a structure and various methods that may be useful in calibrating such a tool to thereby eliminate or at least reduce the effects of such errors.

By way of example only, assuming that the feature to be measured has a nominal critical dimension of 100 nm, a scatterometry-based tool may measure many of the features to find that the critical dimension varies from 98–101 nm. However, some of the features may also initially be measured to have a critical dimension of, for example, 93 nm. At that time, the scatterometry-based tool may be calibrated using the array 61 of grating structures 60A–E disclosed herein. More particularly, the scatterometry tool may be used to measure one of the grating structures 60A–E having the closest target feature size to that of the measured dimension. In this case, the scatterometry-based tool may be used to measure the grating structure 60C having a known or target feature size of 90 nm. Based upon the measurement of the grating structure 60C, the scatterometry tool may be calibrated. That is, if, in measuring the grating structure 60C (of a known value of 90 nm), the tool data indicates a value of 91, then the tool may be calibrated based upon this data by multiplying the measurement data for the measured feature by a correction factor based upon the measurement data of the grating structure 60C. That is, a measured value of 93 nm would be properly calibrated to be 93 nm×(91/

90)=94.03 nm. While such errors in measurement may be very small in absolute terms, in the context of forming integrated circuit devices to the dimensions of modern devices, it may be critically important to accurately determine the size or critical dimension of the resulting features and to determine the efficiency of the processes used to manufacture such devices.

A variety of scatterometry tools 74 may be used with the present invention, e.g., so-called 2θ-type systems and lens-type scatterometry tools. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The optical characteristic traces generated by the scatterometry tool 74 may be based upon a comparison of light intensity to wavelength (for white light, fixed angle type scatterometry tools) or a comparison of intensity to incident angle (for angle resolved systems that use a single light source). Additionally, the light source 73 and the detector 75 may be arranged in a concentric circle configuration, with the light source 73 illuminating the grating structures 60A–E from a perpendicular orientation, e.g., a reflectometer. The intensity of the reflected light may be measured as s- and p-polarization over either multiple angles or at multiple wavelengths.

In general, the scatterometry tool 74 (see FIG. 4A) includes optical hardware, such as an ellipsometer or reflectometer, and a data processing unit loaded with a scatterometry software application for processing data collected by the optical hardware. For example, the optical hardware may include a Model OP5230 or OP5240 with a spectroscopic ellipsometer offered by Thermawave, Inc. of Fremont, Calif. The data processing unit may comprise a profile application server manufactured by Timbre Technologies, a fully owned subsidiary of Tokyo Electron America, Inc. of Austin, Tex. and distributed by Thermawave, Inc.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

The present invention is generally directed to a method and a structure for calibrating a scatterometry-based metrology tool used to measure dimensions of features on a semiconductor device. In one illustrative embodiment, the method comprises measuring a critical dimension of at least one production feature formed above a wafer using a scatterometry tool, measuring at least one of a plurality of grating structures formed above the wafer using the scatterometry tool, each of the grating structures having a different critical dimension, and correcting the measured critical dimension of the at least one production feature based upon the measurement of the at least one grating structure.

In another illustrative embodiment, the method comprises forming a plurality of production features above a wafer, forming a plurality of grating structures above the wafer, each of the grating structures comprised of a plurality of features each having a target critical dimension that thereby defines a critical dimension of the grating structure, each of the grating structures having a different critical dimension, measuring a critical dimension of at least one of the production features using a scatterometry tool, measuring at least one of the grating structures using the scatterometry tool to determine a measured critical dimension of at least one feature of the at least one grating structure, and correcting the measured critical dimension of the at least one production feature based upon a comparison between the measured critical dimension of the at least one feature on the at least one grating structure and the target critical dimension of the feature on the at least one grating structure.

Through use of the present invention, better metrology data may be obtained in the course of manufacturing integrated circuit devices. The present invention may also be useful in determining the efficiency of various processes performed in manufacturing integrated circuit devices. In general, the present invention may result in improving device performance and increasing production yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method, comprising:
    measuring a critical dimension of at least one production feature formed above a wafer using a scatterometry tool;
    measuring at least one of a plurality of grating structures formed above said wafer using said scatterometry tool, each of said grating structures having a different critical dimension; and
    correcting said measured critical dimension of said at least one production feature based upon said measurement of said at least one of said grating structures.

2. The method of claim 1, wherein measuring a critical dimension of at least one production feature formed above a wafer using a scatterometry tool comprises illuminating said at least one production feature and measuring light reflected off of said at least one production feature using said scatterometry tool.

3. The method of claim 1, wherein measuring a critical dimension of at least one production feature formed above a wafer using a scatterometry tool comprises measuring a critical dimension of at least one production feature formed above a wafer using a scatterometry tool, said production feature comprised of at least one of a shallow trench isolation, a gate electrode structure and a conductive line.

4. The method of claim 1, wherein measuring a critical dimension of at least one production feature formed above a wafer using a scatterometry tool comprises measuring a critical dimension of at least one production feature formed above a wafer using a scatterometry tool comprised of a light source and a detector.

5. The method of claim 1, wherein measuring at least one of a plurality of grating structures formed above said wafer using said scatterometry tool, each of said grating structures having a different critical dimension, comprises measuring at least one of a plurality of grating structures formed above said wafer using said scatterometry tool, each of said grating structures having a different critical dimension, a first of said plurality of grating structures having a critical dimension of a first size, at least one of said plurality of grating structures having a critical dimension of a second size, said second size being greater than said first size, the remainder of said plurality of grating structures having a critical dimension that is less than said first size.

6. The method of claim 1, wherein measuring at least one of a plurality of grating structures formed above said wafer using said scatterometry tool, each of said grating structures having a different critical dimension, comprises measuring at least one of a plurality of grating structures formed above said wafer using said scatterometry tool, each of said grating structures having a different critical dimension, said critical dimensions of said grating structures varying from one another by a fixed increment.

7. The method of claim 1, wherein measuring at least one of a plurality of grating structures formed above said wafer using said scatterometry tool, each of said grating structures having a different critical dimension, comprises measuring at least one of five grating structures formed above said wafer using said scatterometry tool, each of said grating structures having a different critical dimension.

8. The method of claim 1, wherein measuring at least one of a plurality of grating structures formed above said wafer using said scatterometry tool, each of said grating structures having a different critical dimension, comprises illuminating said at least one grating structure and measuring light reflected off of said at least one grating structure using said scatterometry tool.

9. A method, comprising:
measuring a critical dimension of at least one production feature formed above a wafer using a scatterometry tool;
measuring at least one of a plurality of grating structures formed above said wafer using said scatterometry tool, each of said grating structures having a different critical dimension, said critical dimension of each of said grating structures being defined by a critical dimension of features that comprise said grating structure; and
correcting said measured critical dimension of said at least one production feature based upon said measurement of said at least one of said grating structures.

10. The method of claim 9, wherein measuring a critical dimension of at least one production feature formed above a wafer using a scatterometry tool comprises illuminating said at least one production feature and measuring light reflected off of said at least one production feature using said scatterometry tool.

11. The method of claim 9, wherein measuring a critical dimension of at least one production feature formed above a wafer using a scatterometry tool comprises measuring a critical dimension of at least one production feature formed above a wafer using a scatterometry tool, said production feature comprised of at least one of a shallow trench isolation, a gate electrode structure and a conductive line.

12. The method of claim 9, wherein measuring a critical dimension of at least one production feature formed above a wafer using a scatterometry tool comprises measuring a critical dimension of at least one production feature formed above a wafer using a scatterometry tool comprised of a light source and a detector.

13. The method of claim 9, wherein measuring at least one of a plurality of grating structures formed above said wafer using said scatterometry tool, each of said grating structures having a different critical dimension, comprises measuring at least one of a plurality of grating structures formed above said wafer using said scatterometry tool, each of said grating structures having a different critical dimension, a first of said plurality of grating structures having a critical dimension of a first size, at least one of said plurality of grating structures having a critical dimension of a second size, said second size being greater than said first size, the remainder of said plurality of grating structures having a critical dimension that is less than said first size.

14. The method of claim 9, wherein measuring at least one of a plurality of grating structures formed above said wafer using said scatterometry tool, each of said grating structures having a different critical dimension, comprises measuring at least one of a plurality of grating structures formed above said wafer using said scatterometry tool, each of said grating structures having a different critical dimension, said critical dimensions of said grating structures varying from one another by a fixed increment.

15. The method of claim 9, wherein measuring at least one of a plurality of grating structures formed above said wafer using said scatterometry tool, each of said grating structures having a different critical dimension, comprises measuring at least one of five grating structures formed above said wafer using said scatterometry tool, each of said grating structures having a different critical dimension.

16. The method of claim 9, wherein measuring at least one of a plurality of grating structures formed above said wafer using said scatterometry tool, each of said grating structures having a different critical dimension, comprises illuminating said at least one grating structure and measuring light reflected off of said at least one of said grating structures using said scatterometry tool.

17. A method, comprising:
measuring a critical dimension of at least one production feature formed above a wafer using a scatterometry tool;
measuring at least one of a plurality of grating structures formed above said wafer using said scatterometry tool, each of said grating structures having a different critical dimension, said critical dimension of each of said grating structures being defined by a critical dimension of features that comprise said grating structure, said critical dimensions of said grating structures varying from one another by a fixed increment, a first of said plurality of grating structures having a critical dimension of a first size that is a nominal critical dimension for said at least one production feature, at least one of said plurality of grating structures having a critical dimension of a second size, said second size being greater than said first size, the remainder of said plurality of grating structures having a critical dimension that is less than said first size; and correcting said measured critical dimension of said at least one production feature based upon said measurement of said at least one of said grating structures.

18. The method of claim 17, wherein measuring a critical dimension of at least one production feature formed above a wafer using a scatterometry tool comprises illuminating said at least one production feature and measuring light reflected off of said at least one production feature using said scatterometry tool.

19. The method of claim 17, wherein measuring a critical dimension of at least one production feature formed above a wafer using a scatterometry tool comprises measuring a critical dimension of at least one production feature formed above a wafer using a scatterometry tool, said production feature comprised of at least one of a shallow trench isolation, a gate electrode structure and a conductive line.

20. The method of claim 17, wherein measuring a critical dimension of at least one production feature formed above a wafer using a scatterometry tool comprises measuring a critical dimension of at least one production feature formed above a wafer using a scatterometry tool comprised of a light source and a detector.

21. The method of claim 17, wherein measuring at least one of a plurality of grating structures formed above said wafer using said scatterometry tool, each of said grating structures having a different critical dimension, comprises measuring at least one of five grating structures formed above said wafer using said scatterometry tool, each of said grating structures having a different critical dimension.

22. The method of claim 17, wherein measuring at least one of a plurality of grating structures formed above said wafer using said scatterometry tool, each of said grating structures having a different critical dimension, comprises illuminating said at least one grating structure and measuring light reflected off of said at least one of said grating structures using said scatterometry tool.

23. A method, comprising:

forming a plurality of production features above a wafer;

forming a plurality of grating structures above said wafer, each of said grating structures comprised of a plurality of features each having a target critical dimension that thereby defines a critical dimension of said each of said grating structures, each of said grating structures having a different critical dimension;

measuring a critical dimension of at least one of said production features using a scatterometry tool;

measuring at least one of said grating structures using said scatterometry tool to determine a measured critical dimension of at least one feature of at least one of said grating structures; and correcting said measured critical dimension of said at least one production feature based upon a comparison between said measured critical dimension of said at least one feature on said at least one of said grating structures and said target critical dimension of said feature on said at least one grating structure.

24. The method of claim 23, wherein forming a plurality of production features above a wafer comprises forming a plurality of production features above a wafer, said production features comprised of at least one of a shallow trench isolation, a gate electrode structure and a conductive line.

25. The method of claim 23, wherein each of said grating structures is comprised of a plurality of at least one of a shallow trench isolation, a gate electrode structure and a conductive line.

26. The method of claim 23, wherein said grating structures have a different critical dimension that varies by a fixed increment.

27. The method of claim 23, wherein measuring a critical dimension of at least one of said production features using a scatterometry tool comprises illuminating and measuring light reflected off of said at least one of said production features using said scatterometry tool.

28. The method of claim 23, wherein measuring at least one of said grating structures using said scatterometry tool to determine a measured critical dimension of at least one feature of said at least one of said grating structures comprises illuminating and measuring light reflected off of said at least one of said grating structures using said scatterometry tool.

29. The method of claim 23, wherein measuring a critical dimension of at least one production feature formed above a wafer using a scatterometry tool comprises measuring a critical dimension of at least one production feature formed above a wafer using a scatterometry tool, said production feature comprised of at least one of a shallow trench isolation, a gate electrode structure and a conductive line.

30. The method of claim 23, wherein measuring a critical dimension of at least one of said production features formed above a wafer using a scatterometry tool comprises measuring a critical dimension of at least one production feature formed above a wafer using a scatterometry tool comprised of a light source and a detector.

31. The method of claim 23, wherein a first of said plurality of grating structures has a critical dimension of a first size, at least one of said plurality of grating structures has a critical dimension of a second size, said second size being greater than said first size, the remainder of said plurality of grating structures having a critical dimension that is less than said first size.

32. The method of claim 23, wherein forming a plurality of grating structures above said wafer comprises forming at least five grating structures above said wafer.

* * * * *